(12) United States Patent
Habara et al.

(10) Patent No.: US 8,947,084 B2
(45) Date of Patent: Feb. 3, 2015

(54) ANTENNA DEVICE AND MAGNETIC RESONANCE IMAGING DEVICE

(75) Inventors: Hideta Habara, Musaashino (JP);
Yoshitaka Bito, Kokubunji (JP); Hisaaki Ochi, Kodaira (JP); Yoshihisa Soutome, Tokyo (JP); Yukio Kaneko, Kawaguchi (JP); Masayoshi Dohata, Yokohama (JP)

(73) Assignee: Hitachi Medical Corporation, Tokyo (JP)

( * ) Notice: Subject to any disclaimer, the term of this patent is extended or adjusted under 35 U.S.C. 154(b) by 773 days.

(21) Appl. No.: 13/125,829

(22) PCT Filed: Jul. 22, 2009

(86) PCT No.: PCT/JP2009/063110
§ 371 (c)(1),
(2), (4) Date: Apr. 25, 2011

(87) PCT Pub. No.: WO2010/050279
PCT Pub. Date: May 6, 2010

(65) Prior Publication Data
US 2011/0204890 A1    Aug. 25, 2011

(30) Foreign Application Priority Data

Oct. 29, 2008  (JP) .................................. 2008-278059

(51) Int. Cl.
*G01R 33/44*    (2006.01)
*H01Q 9/04*    (2006.01)
(Continued)

(52) U.S. Cl.
CPC .... *G01R 33/34046* (2013.01); *G01R 33/34053* (2013.01); *G01R 33/34061* (2013.01); *G01R 33/341* (2013.01); *A61B 5/055* (2013.01); *G01R 33/34007* (2013.01)
USPC ...... 324/307; 324/318; 324/322; 343/700 MS

(58) Field of Classification Search
USPC .................................................. 324/307, 318
See application file for complete search history.

(56) References Cited

U.S. PATENT DOCUMENTS 4,751,464 A    6/1988  Bridges
5,467,017 A    11/1995 Duerr et al.
(Continued)

FOREIGN PATENT DOCUMENTS

JP    2-95347 A    4/1990
JP    7-372 A      1/1995
(Continued)

OTHER PUBLICATIONS

Streif, Jorg Ulrich; "European Search Report for EP 09823392" peformed on Mar. 28, 2013, all pages.*
(Continued)

*Primary Examiner* — Melissa Koval
*Assistant Examiner* — Rishi Patel
(74) *Attorney, Agent, or Firm* — Mattingly & Malur, PC

(57) ABSTRACT

Manufacture cost and maintenance cost of RF coils of MRI devices are reduced without any limitation concerning size of the coils. By constituting an antenna device for magnetic resonance imaging devices with a cylindrical outer conductor, a looped ribbon-shaped conductor disposed inside the cylindrical outer conductor along the cylindrical surface, and a feed point for transmission and/or reception between the cylindrical conductor and the ribbon-shaped conductor, and disposing the ribbon-shaped conductor so that length thereof can be readily adjusted, there is provided an antenna device for magnetic resonance imaging devices that generates a magnetic field component perpendicular to the central axis of the cylinder at a desired resonance frequency and shows sensitivity without using capacitors and without being imposed any limitation concerning size in the diametral direction of the cylinder.

13 Claims, 15 Drawing Sheets

(51) Int. Cl.
*G01R 33/34* (2006.01)
*G01R 33/341* (2006.01)
*A61B 5/055* (2006.01)

(56) References Cited

U.S. PATENT DOCUMENTS

| | | | |
|---|---|---|---|
| 5,557,247 | A | 9/1996 | Vaughn, Jr. |
| 6,100,694 | A | 8/2000 | Wong |
| 6,498,487 | B1 | 12/2002 | Haner |
| 2002/0079996 | A1 | 6/2002 | Zhang et al. |
| 2005/0040823 | A1 | 2/2005 | Blumich et al. |
| 2006/0006865 | A1 | 1/2006 | Zhang et al. |
| 2007/0247160 | A1* | 10/2007 | Vaughan, Jr. .......... 324/322 |

FOREIGN PATENT DOCUMENTS

| | | |
|---|---|---|
| JP | 2001-145610 A | 5/2001 |
| JP | 2004-511278 A | 4/2004 |
| JP | 2006-136388 A | 6/2006 |
| JP | 2008526273 | 7/2008 |
| WO | 2004/038442 A2 | 5/2004 |
| WO | 2006/067746 A2 | 6/2006 |

OTHER PUBLICATIONS

C. Hayes et al., An Efficient, Highly Homogeneous Radiofrequency Coil for Whole-Body NMR Imaging at 1.5 T, Journal of Magnetic Resonance, 63, pp. 622-628, 1985.

Z. Zhai et al., Ring Structured RF Coils for Ultra-High Field MRI, Proceedings of International Society for Magnetic Resonance in Medicine, 15, p. 3276, 2007.

N.I. Avdievich et al., 4T Split TEM Volume Head and Knee Coils for Improved Sensitivity and Patent Comfort, Proc. Intl. Soc. Mag. Reson. Med., 14, p. 2609, 2006.

* cited by examiner 1301    1302    1303

180
ANTENNA DEVICE AND MAGNETIC RESONANCE IMAGING DEVICE

TECHNICAL FIELD

The present invention relates to an antenna device for transmitting and receiving electromagnetic waves, and a magnetic resonance imaging device (henceforth referred to as MRI device) using the same.

BACKGROUND ART

MRI devices irradiate electromagnetic waves on a subject placed in a uniform static magnetic field generated by a magnet to excite nuclear spins in the subject and receive magnetic resonance signals as electromagnetic waves generated by the nuclear spins for imaging the subject. The irradiation of the electromagnetic waves and the reception of the magnetic resonance signals are attained by a device called RF antenna or RF coil, which transmits or receives radio frequency (RF) electromagnetic waves.

RF coils or antennas are roughly classified into two groups, those called surface antennas or local antennas and those called volume coils or volume antennas. Surface antennas have a round shape or planar shape, and show sensitivity in neighborhood of the antennas, and upon use, they are put on the surface of the subject. The volume antennas have a cylindrical shape or a two-disc shape consisting of two discs disposed up and down, and they show sensitivity in the whole space in the cylinder or between the discs, and upon use, a subject is placed in the space.

Among the volume antennas, those having a cylindrical shape are used in MRI devices called those of tunneled type, with which imaging is performed by entering a human lying on a bed into the inside of the magnet having a cylindrical shape. On the other hand, those in the shape of a pair of upper and lower discs are used in MRI devices called those of vertical magnetic field type, hamburger type or open type, with which imaging is performed by entering a human lying on a bed into the space between the upper and lower magnets.

Volume antennas having a cylindrical shape include those of a type called birdcage type (refer to, for example, Non-patent document 1) and those of a type called TEM type (refer to, for example, Patent documents 1 and 2). These volume antennas are usually provided with about 16 to 24 of rod-shaped conductors called rungs (crosspieces or crossbars of ladder) disposed along the side of the cylinder in parallel to the center axis of the cylinder. Capacitors are disposed in each of the rungs in order to resonate the antenna at the frequency of the electromagnetic wave irradiated on the subject. The number of capacitors to be disposed is usually at least 2×M, or about 6×M in the case of those having a larger number of capacitors, where M represents the number of rungs. For example, in the case of a birdcage type volume antenna having 24 of rungs, 24×6=144 of capacitors are used to constitute the antenna. As the number of capacitors increases, production cost and cost for quality control at the time of maintenance thereof increase.

As an attempt to reduce the number of capacitors aiming at reduction of the production and maintenance costs, there is an RF coil configured so that reception points are provided between a large ground plane and a ribbon-shaped conductor disposed with a distance from the ground plane (refer to, for example, Patent document 3). With such a configuration, a certain level of electric capacitance is effectually provided between the large ground plane and the ribbon-shaped conductor even if capacitors are not disposed between them as lumped elements, and therefore the number of capacitors can be reduced compared with an RF coil configured in a usual manner.

Although the technique disclosed in Patent document 3 is fundamentally directed to surface antennas, there is also described an example of volume antenna constituted with a large ground plane and a ribbon-shaped conductor in Patent document 3. In this example, the ring portions of the birdcage type antenna can be regarded as a large ground plane in the shape of divided two cylinders, and it is also regarded that rung portions are replaced with the ribbon-shaped conductor. Therefore, the fundamental configuration thereof is the same as that of a birdcage type antenna. However, in this volume antenna, the two cylindrical conductors carry out the same function as that of the ring portions of the birdcage type antenna, and therefore the cylindrical conductors do not serve as a perfect RF shield. As a result, the antenna shows sensitivity in the outside of the antenna having a cylindrical shape. Accordingly, when a conductor or a subject approaches from outside of the antenna, the sensitivity of the antenna significantly changes, and thus it is not suitable for practical use. Moreover, in this volume antenna, thickness of the dielectric material is a large factor for determining the resonance frequency, and therefore adjustment of the frequency is also difficult.

As an example of volume antenna having a reduced number of capacitors and not showing sensitivity in the outside of the antenna, there is a volume antenna having a large cylindrical ground plane, ring-shaped ground planes disposed at the positions of upper and lower openings of the cylinder and contacting with the cylindrical ground plane, and rings constituted with ribbon-shaped conductors disposed inside of the ring-shaped ground planes (refer to, for example, Non-patent document 2).

PRIOR ART REFERENCES

Patent Documents

Patent document 1: U.S. Pat. No. 4,751,464
Patent document 2: U.S. Pat. No. 5,557,247
Patent document 3: Japanese Patent Application No. 2002-534856

Non-Patent Document

Non-patent document 1: Cecil E. Hayes, et al., "An Efficient, Highly Homogeneous Radiofrequency Coil for Whole-Body NMR Imaging at 1.5 T", Journal of Magnetic Resonance, 63:622-628 (1985)
Non-patent document 2: Z. Zhai, et al., "Ring Structured RF Coils for Ultra-High Field MRI", Proceedings of International Society for Magnetic Resonance in Medicine, 2007, p. 3276

SUMMARY OF THE INVENTION

Problem to be Solved by the Invention

However, the technique disclosed in Non-patent document 2 suffers from a limitation that the length of the circumference of the ring portion must be effectually equal to the length of the wavelength used by the antenna, and therefore practical size of the antenna is limited by the intensity of the magnetic field used in the MRI device. For example, in the case of MRI device of 7 teslas, it is applicable only to a volume antenna of the size for the human head.

The present invention was accomplished in light of the above-mentioned circumstances, and an object of the present invention is to provide a technique concerning RF coil of MRI device for eliminating the limitation on size and enabling reduction of production and maintenance costs.

Means to Solve the Problem

The present invention provides an antenna device for magnetic resonance imaging devices having a cylindrical outer conductor, a looped ribbon-shaped conductor disposed inside the cylindrical outer conductor along the cylindrical shape, and a feed point for transmission and/or reception disposed between the cylindrical outer conductor and the ribbon-shaped conductor, wherein the ribbon-shaped conductor is disposed so that length of the conductor can be readily adjusted, and thus the antenna device generates a magnetic field component perpendicular to the center axis of the cylinder at a desired resonance frequency without using capacitor and without suffering from a limitation concerning size in the diametral direction of the cylinder, and shows sensitivity in the inside of the cylinder.

Specifically, the present invention provides An antenna device used for transmission and/or reception of a signal comprising: a cylindrical conductor having a cylindrical shape, a ribbon-shaped conductor having a length in the direction of the conductor longer than circumference of cylinder of the cylindrical conductor, and a transmission and reception means connected to the cylindrical conductor and the ribbon-shaped conductor, which transmits and receives signals to and from the antenna device, wherein: the ribbon-shaped conductor is disposed on the cylindrical surface inside of the cylindrical conductor in the form of loop so as to generate a magnetic field having a component perpendicular to central axis of the cylindrical conductor in the inside of the cylindrical conductor.

Effect of the Invention

According to the present invention, the limitation concerning size of RF coil of MRI device is eliminated, and production and maintenance costs can be reduced.

MODES FOR CARRYING OUT THE INVENTION

<<First Embodiment>>

Hereafter, the first embodiment of the present invention will be explained. In all of the drawings for explaining the embodiments of the present invention, elements having the same function are indicated with the same numerals or symbols, and repetition of the explanations thereof are omitted.

Figure 1:
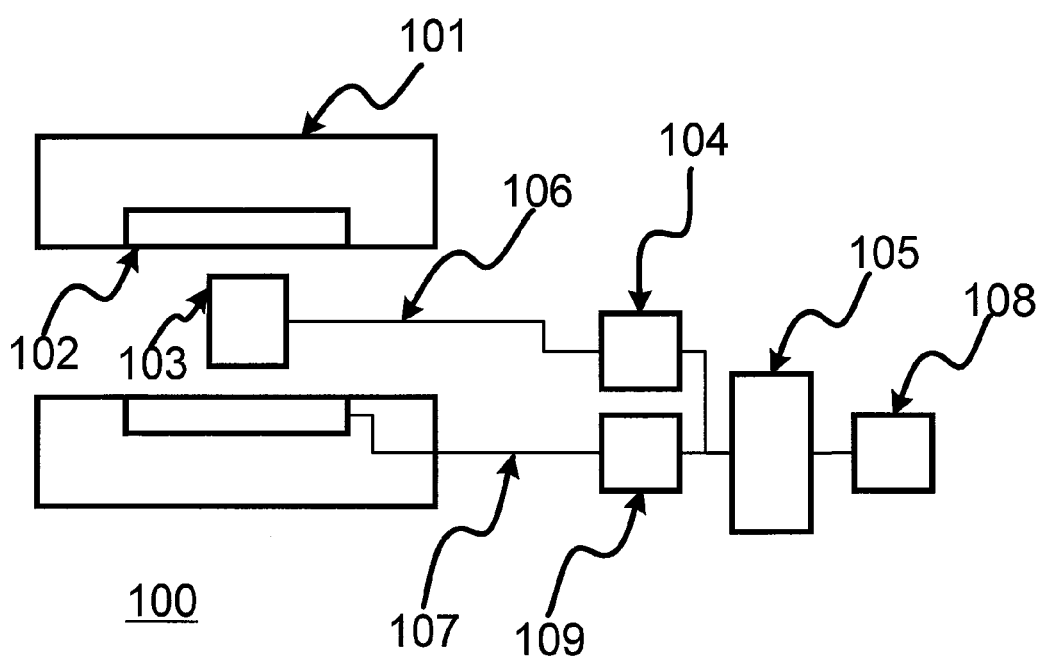
FIG. 1 shows schematic configuration of an MRI device according to an embodiment of the present invention.

First, configuration of an MRI device of this embodiment will be explained. FIG. 1 is a drawing showing schematic configuration of an MRI device 100 according to this embodiment. The MRI device 100 is provided with a magnet 101 for applying a static magnetic field to a subject, a gradient coil 102 for imparting magnetic field gradient to the static magnetic field in a predetermined direction, an RF coil 103 inserted into the inside of the magnet 101, which is for transmitting electromagnetic waves such as radio frequency waves to the subject and receiving electromagnetic waves, a transceiver 104 connected to the RF coil 103, which is for creating and transmitting electromagnetic waves to be irradiated from the RF coil 103, detecting nuclear magnetic resonance signals transmitted from the RF coil 103, and processing the signals, a gradient magnetic field power supply 109 for supplying an electric current to the gradient coil 102, a data processing part 105 for controlling driving of the transceiver 104 and the gradient magnetic field power supply 109 and executing various information processings and operations directed by an operator, and a display 108 for displaying processing results obtained by the data processing part 105.

The gradient magnetic field power supply 109 and the gradient coil 102 are connected with a gradient magnetic field control cable 107. Further, the RF coil 103 and the transceiver 104 are connected with a cable for controlling the RF coil 103 and a transmission and reception cable 106. The transceiver 104 is provided with a synthesizer, a power amplifier, a reception mixer, an analog to digital converter, a transmission and reception changeover switch, and so forth, although they are not shown in the drawing.

The MRI device 100 may be of the horizontal magnetic field type or the vertical magnetic field type according to the direction of the static magnetic field generated by the magnet 101. In the case of the horizontal magnetic field type, the magnet 101 generally has a cylindrical boa (central space), and generates a static magnetic field of the horizontal direction in FIG. 1. In the case of the vertical magnetic field type, a pair of magnets is disposed up and down on both sides of the subject, and they generate a static magnetic field of the vertical direction in FIG. 1. The MRI device 100 of this embodiment may be of either of these types. Hereafter, explanation will be made by exemplifying a device of the horizontal magnetic field type.

In the MRI device 100, the RF coil 103 and the gradient coil 102 irradiate a series of intermittent electromagnetic waves and gradient magnetic fields at intervals of about several milliseconds to the subject (not shown) placed in the static magnetic field, and signals generated from the subject by resonance with the electromagnetic waves are received and processed to obtain magnetic resonance images. Although the single RF coil 103 is shown in this drawing as the RF coil for irradiation and reception of electromagnetic waves, there may be used an RF coil consisting of a plurality of coils, for example, a combination of an RF coil for imaging of wide range and an RF coil for local imaging.

Figure 2:
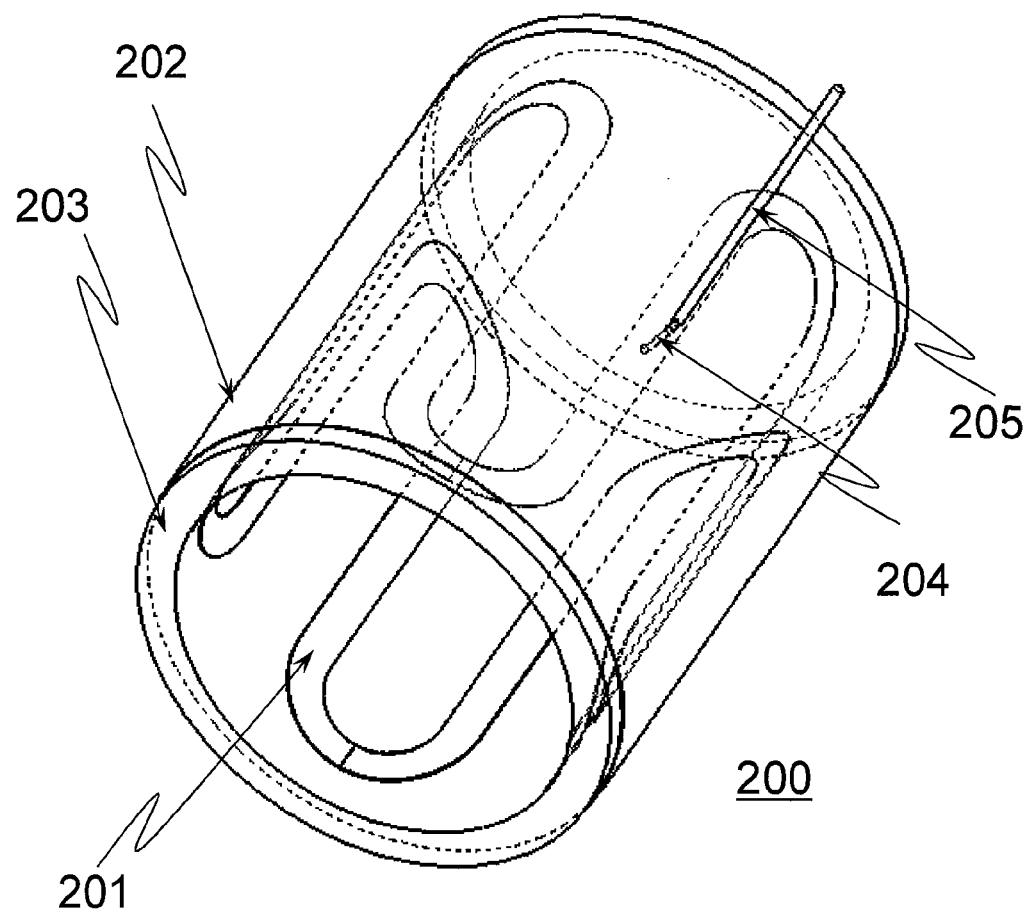
FIG. 2 shows an external view of a volume antenna according to an embodiment of the present invention.

The RF coil 103 (volume antenna) of this embodiment will be explained below. In this embodiment, a characteristically bent loop coil consisting of a conductor having a predetermined width is combined with a shield to form a volume antenna 200, which does not use capacitor, and is free from limitation on size. For the MRI device 100 of the horizontal magnetic field type, the volume antenna 200 having a cylindrical shape is used. FIG. 2 shows an external view of the volume antenna 200 of this embodiment. The volume antenna 200 of this embodiment is provided with a conductor 201 having a predetermined width, a conductor 202 having a cylindrical shape (cylindrical conductor 202) functioning as a ground plane, and a housing 203 having a cylindrical shape. The cylindrical conductor 202 is adhered on the external surface of the housing 203 so that it has the same central axis as that of the housing 203. The conductor 201 is adhered on the internal surface of the housing 203 so that it is looped and making a circuit around the internal cylindrical surface of the housing 203. The conductor 201 has such a shape that an electric capacitance is formed between the conductor 201 and the conductor 202, for example, a ribbon shape having a width. The conductor 201 is called ribbon-shaped conductor 201 hereafter.

Further, the volume antenna 200 of this embodiment is provided with a connection point 204, which is connected to a coaxial cable 205 as a means for transmitting and/or receiving RF signals. A outer conductor (also called external conductor) of the coaxial cable 205 is connected to the cylindrical conductor 202 of the volume antenna 200, and a inner conductor of the coaxial cable 205 is lead into the inside through holes provided on the cylindrical conductor 202 and the housing 203, and connected to the ribbon-shaped conductor 201. The connection point 204, which is connection part of the outer conductor of the coaxial cable 205 and the cylindrical conductor 202, and connection part of the inner conductor of the coaxial cable 205 and the ribbon-shaped conductor 201, is called transmission and/or reception point 204. In addition, the "transmission and/or reception point" 204 is generally also called "feed point and/or receiving point", and when it is not necessary to be particularly distinguished, it is called feed point 204 in this specification.

Figure 3:
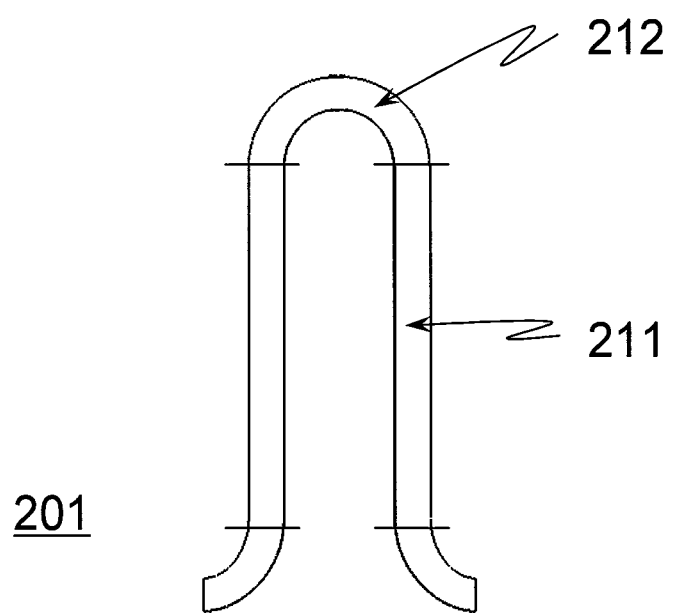
FIG. 3 shows a part of the ribbon-shaped conductor of a volume antenna according to an embodiment of the present invention.

Further, the ribbon-shaped conductor 201 of the volume antenna 200 of this embodiment is disposed so that it resonates at the frequency of the electromagnetic waves as the object of transmission and reception, and generates a highly uniform magnetic field component in the inside of the cylinder (henceforth simply called as cylinder) formed by the cylindrical conductor 202 and the housing 203 in a direction perpendicular to the central axis of the cylinder, regardless of the size of the housing 203. FIG. 3 shows a part of the ribbon-shaped conductor 201 of the volume antenna 200 of this embodiment. As shown in this drawing, the ribbon-shaped conductor 201 of this embodiment is provided with a plurality of straight portions 211 disposed in parallel to the cylindrical axis and a plurality of arc portions 212 connecting the straight portions. The straight portions 211 correspond to rung portions of a birdcage type antenna or TEM type antenna. Therefore, length L of the whole ribbon-shaped conductor 201 becomes longer than the circumference of the inner surface of the cylinder. Under such a condition, the length L of the ribbon-shaped conductor 201 is adjusted to such a length that the antenna resonates at the frequency f of the electromagnetic wave of transmission and reception, and generates a highly uniform magnetic field component in the inside thereof.

The length L of the ribbon-shaped conductor 201 satisfying the aforementioned condition will be explained below. First, the condition of the length L for the resonance at the frequency f of the electromagnetic wave to be transmitted and received is explained. In the case of a conductor connected as a loop and forming a closed curve, like the ribbon-shaped conductor 201 of this embodiment, if the effectual length thereof is represented by L', and the length L' is natural number of times the wavelength $\lambda$ of the electromagnetic wave to be transmitted and received, a stable standing wave can be obtained. That is, when the length satisfies the condition: $L'=n \times \lambda_n$ (n is a natural number, henceforth called wave number), a standing wave is generated for an electromagnetic wave of a wavelength $\lambda_n$, and resonation occurs.

In general, if there is a ground plane having a large area, a ribbon-shaped conductor connected in a loop shape is disposed at a distance from the ground plane, and a feed point is provided between the ribbon-shaped conductor and the ground plane, the effectual length of the ribbon-shaped conductor corresponds to a value obtained by dividing the length of the ribbon-shaped conductor along the conductor by the specific propagation velocity ratio for the ribbon-shaped conductor regarded as propagation line with respect to the velocity of light in a free space (or vacuum) c.

If the length of the ribbon-shaped conductor 201 of this embodiment along the conductor is L, and the specific propagation velocity ratio is A, the effectual length L' of the ribbon-shaped conductor 201 is represented as L/A. Therefore, when the length L of the ribbon-shaped conductor 201 and the wavelength in a vacuum $\lambda$ of the electromagnetic wave supplied from the feed point 204 satisfy the relation of $L/A=n \times \lambda$, a standing wave is generated in the ribbon-shaped conductor 201, and resonation occurs. Therefore, when the frequency of the electromagnetic wave as the object of transmission and reception is f, the length L of the ribbon-shaped conductor 201 is adjusted so as to satisfy at least the following equation (1).

$$L = n \times A \times (c/f) \quad (1)$$

Figure 4:
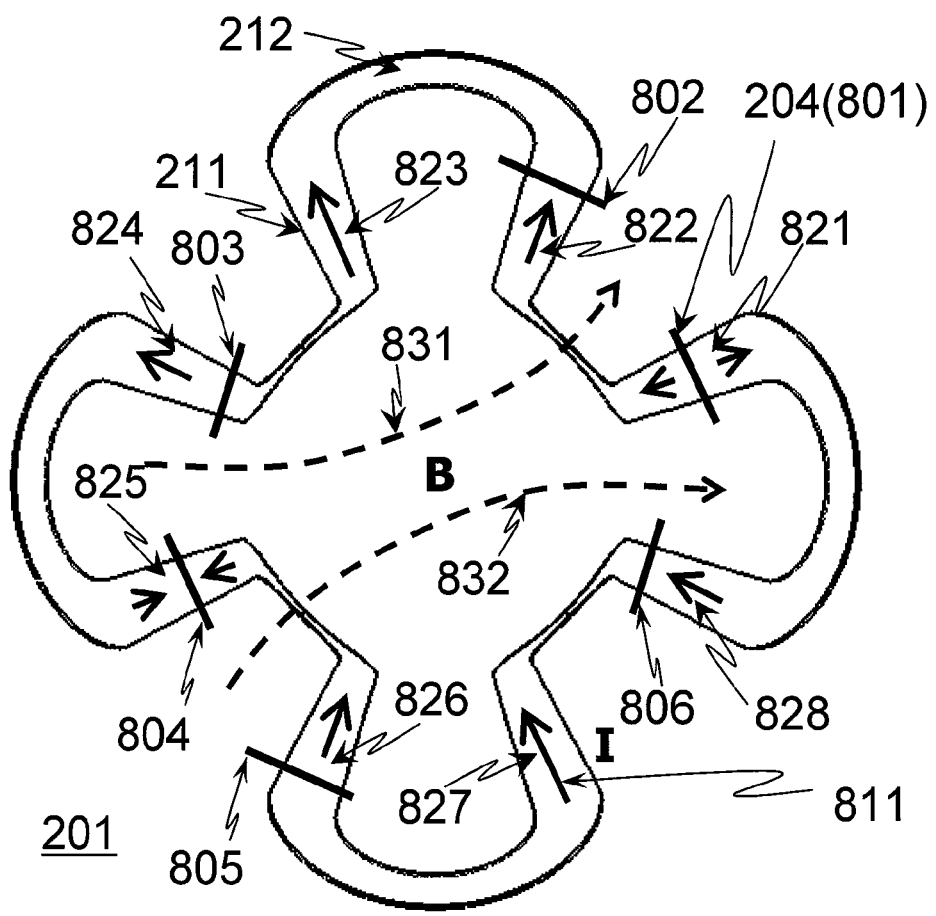
FIG. 4 is a drawing for explaining a magnetic field generated when the ribbon-shaped conductor according to an embodiment of the present invention resonates.

The length for generating a highly uniform magnetic field in the inside of the cylinder within the range of L satisfying the aforementioned equation (1) is examined below. FIG. 4 is a drawing for explaining a magnetic field generated by the volume antenna 200 in the inside thereof, and it is a perspective view of the ribbon-shaped conductor 201 disposed in the inside of the volume antenna 200 seen from one opening of the cylinder. Here, explanation will be made by exemplifying the volume antenna 200 having 8 of the straight portions 211 and 8 of the arc portions 212. That is, the explanation will be made by exemplifying a case where there are eight portions corresponding to rung portions. Further, the feed point 204 is provided in the middle of one of the straight portions 211. It is sufficient that the numbers of the straight portions 211 and the arc portions 212 are 4 or larger.

When the wave number of the generated standing wave is represented by n, this standing wave has 2n of current nodes in the ribbon-shaped conductor 201 at equal intervals, one of which nodes is at the feed point 204. That is, for example, when the wave number n is 3, it has the feed point 204 (node 801), and a node 804 at a distance of L/2 from the feed point 204, as well as nodes 802, 803, 805, and 806 between the nodes 801 and 804 at equal intervals as shown in FIG. 4. Since the directions of electric currents flowing in the ribbon-shaped conductor 201 on both sides of each node are reverse to each other, directions of electric current at a certain moment are as indicated with arrows 811. The directions of the electric current indicated with the arrows 811 are directions of the electric current at a certain moment, and are all reversed at other moments a half cycle before and after that.

When the number of the straight portions 211 is 2N (N is a natural number), if N is equal to the aforementioned wave number n (N=n), the number of nodes and the number of rungs become equal to each other. In this case, although they are in good symmetry, the electric current flows in the rungs in the same direction with respect to the central axis at a certain moment. As a result, direction of the magnetic field generated by the electric current flowing through the rungs is the direction along the circumference of the cylinder, and at the center of the cylinder, contributions of the electric current from all the rungs are canceling out, and become zero. The magnetic field required for MRI devices is a magnetic field that is uniform in the inside of the cylinder and of a direction perpendicular to the axis of the cylinder. In particular, a magnetic field needs to be generated in a certain direction at the center of the cylinder. This can be realized by shifting the wave number n to be used from N by 1. If the wave number n is shifted from N by 1, the directions of electric current flowing in a certain rung and another facing rung at a position shifted by 180 degrees with respect to the center of the cylindrical axis become reverse to each other. When the directions of electric currents flowing in rungs facing each other are reverse to each other with respect to the direction of the central axis, the canceling out of contributions at the central part of the cylinder does not occur, and a magnetic field is generated in a certain direction also at the center of the cylinder. That is, when N and n are in the relationship represented by the following equation (2), a highly uniform magnetic field is generated in the inside of the cylinder.

$$n = N \pm 1 \quad (2)$$

Hereafter, explanation will be made by referring to a specific example. First, it will be explained that, in the aforementioned volume antennas 200 where the number of the straight portions 211 is 8, when the wave number n is 4±1, i.e., 3 or 5, a highly uniform magnetic field is generated in the inside of the cylinder.

As shown in FIG. 4, among the eight straight portions 211 serving as the rungs, in three of them shown in upper left in the drawing, the electric current flows in the straight portions 211 so as to approach the viewing point, and in three of them shown in lower right, it flows so as to go away from the viewing point. Moreover, in one straight portion 211 shown in upper right and one shown in lower left, there is a node in the middle of each straight portion 211, and the electric current flows upward and downward on both sides of the node serving as a border.

Direction of the magnetic field generated by the electric current flowing through these straight portions 211 is considered. The straight portions 211 are numbered 821, 822, 823, 824, 825, 826, 827 and 828 in order, respectively, and the feed point 204 is provided in the middle of the straight portion 821. In this case, in the straight portions 211 other than the straight portion 821 and the straight portion 825, which is at the axially symmetrical position with respect to the central axis of the cylinder, the electric current flows in one direction along the central axis of the cylinder. In the three straight portions 822, 823 and 824 shown in upper left, the electric current flows in the direction toward the viewing point, and therefore the direction of the magnetic field generated by the electric current is the direction indicated with an arrow 831 of broken line going from left to upper right according to the Maxwell's equations. Similarly, the direction of the magnetic field generated by the electric current flowing three lower right straight portions 826, 827 and 828 is the direction indicated with an arrow 832 of broken line going from lower left to right. If they are synthesized, a magnetic field B of a direction from slightly lower left to slightly upper right is generated in the inside of the cylinder.

At the halfway point between the nodes, i.e., the position of so-called antinode, the intensity of the magnetic field becomes maximum, and therefore the magnetic field B is comparatively uniformly generated in the inside of the cylinder. Therefore, when the volume antenna 200 having 8 of the straight portions 211 (i.e., N=4) resonates by generating a standing wave where a wave number n is 3, it generates a uniform magnetic field in the inside of the cylinder, and thus it can be used as the volume antenna 200 of the MRI device 100.

Figure 5:
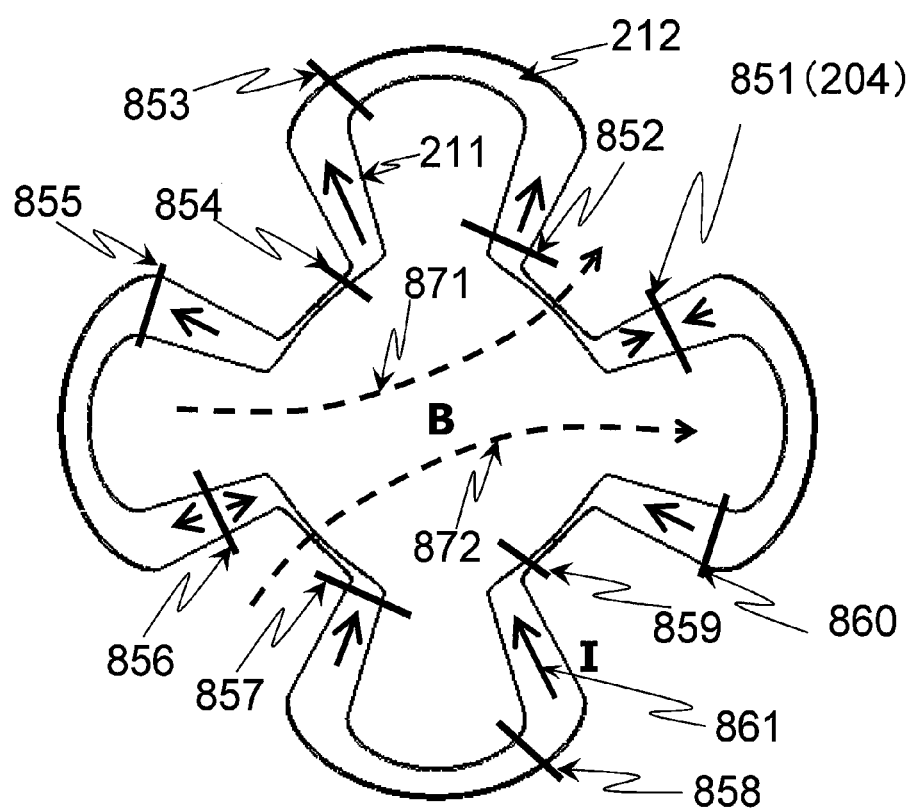
FIG. 5 is a drawing for explaining a magnetic field generated when the ribbon-shaped conductor according to an embodiment of the present invention resonates.

FIG. 5 is a drawing for explaining the magnetic field B generated in the inside of the cylinder of the volume antennas 200 provided with eight of the straight portions 211, when it resonates with a standing wave having a wave number n of 5. As shown in this drawing, when a standing wave having a wave number n of 5 is generated in the volume antenna 200, this standing wave has 10 of nodes 851, 852, 853, 854, 855, 856, 857, 858, 859 and 860. Further, directions of the electric current flowing in each of the straight portions 211 at a predetermined moment are as indicated with arrows 861. The direction of the magnetic field B generated by the electric current in the inside of the cylinder is as indicated with arrows 871 and 872 of the broken lines, and the magnetic field B comparatively uniformly exists in the inside of the cylinder.

Therefore, when the volume antenna 200 provided with eight of the straight portions 211 (N=4) resonates with generating a standing wave having a wave number n of 5, a uniform magnetic field is formed in the inside of the cylinder, and the volume antenna 200 can be used as a volume antenna of the MRI device 100.

In addition, a case where the volume antenna resonates with a standing wave having another wave number is considered. First, when the value of |N−n| is an even number, no magnetic field is produced at the center of the cylinder. When the value of |N−n| is an odd number not smaller than 3, a limited magnetic field is generated in a certain direction at the center of the cylinder. However, a node of the magnetic field is formed at a position inside the cylinder other than the center, and the magnetic field is not uniform. Therefore, resonance generating such a magnetic field is not suitable as a resonance mode of volume antenna used for MRI.

Hereafter, explanation will be made by exemplifying cases where the number of the straight portions 211 is not 8. FIG. 6 includes drawings for explaining states of generation of magnetic field in the inside of the cylinder of the volume antenna 200 having various numbers of the straight portions 211, where the number of the straight portions 211 (2N) and the wave number n of standing wave satisfy the relation defined by the aforementioned equation (2).

Figure 6A:
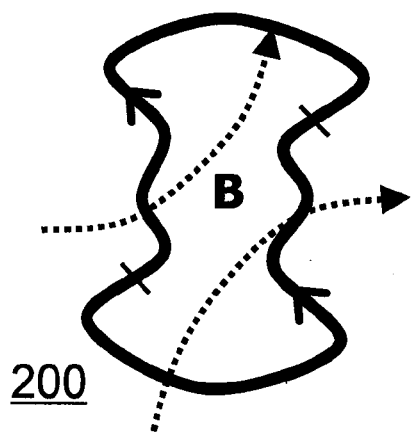
FIG. 6A is a drawing for explaining states of uniform magnetic fields generated inside of the cylinder with a number of straight portions of 4.
Figure 6B:
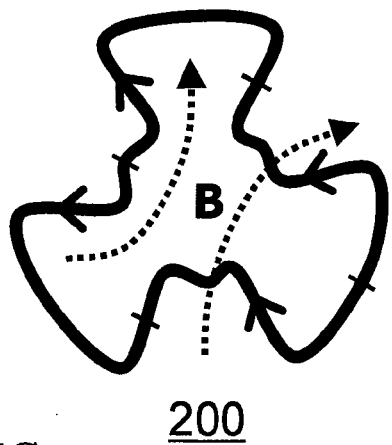
FIG. 6B is a drawing for explaining states of uniform magnetic fields generated inside of the cylinder with a number of straight portions of 6.
Figure 6C:
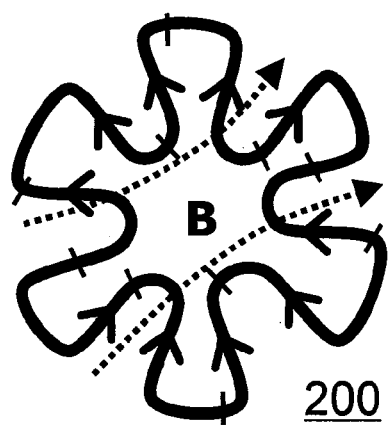
FIG. 6C is a drawing for explaining states of uniform magnetic fields generated inside of the cylinder with a number of straight portions of 12.

FIG. 6A shows the state in the volume antenna 200 of this embodiment where the number of the straight portions 211 corresponding to rungs is 4. FIG. 6B shows the state in the volume antenna 200 where the number is 6. FIG. 6C shows the state in the volume antenna 200 where the number is 12. All the drawings are perspective views of the ribbon-shaped conductor 201 seen from one opening of the cylinder of the volume antenna.

In the volume antennas 200 of FIG. 6A, FIG. 6B, and FIG. 6C, the positions of nodes in the case where the number of the straight portions 211 is 2N, and the resonance occurs with a standing wave having a wave number n of N−1 are indicated with lines crossing the ribbon-shaped conductor 201. Moreover, directions of the electric current flowing through the straight portions 211 at a predetermined moment are indicated with arrows.

As shown in FIG. 6A, in the case of the volume antenna 200 where the number of the straight portions 211 is 4, the wave number of the standing wave is 1, and therefore the number of the nodes is 2. Therefore, when the feed point 204 is provided at the middle point of one straight portion 211, the electric current flows in the two straight portions 211 not having the feed point 204 and facing each other, among the four straight portions 211, in the directions indicated with the arrows shown in the drawing. And a uniform magnetic field B going from the lower left to the upper right is thereby formed in the inside of the cylinder.

Further, as shown in FIG. 6B, in the case of the volume antenna 200 where the number of the straight portions 211 is 6, the wave number of the standing wave is 2, and therefore the number of the nodes is 4. Therefore, when the feed point 204 is provided at the middle point of one straight portion 211, the electric current flows in the four straight portions 211 other than that having the feed point 204 and the straight portion at the position 180 degree rotational symmetric with respect to the center axis of the cylinder, among the 6 straight portions 211, in the directions indicated with the arrows shown in the drawing. And a uniform magnetic field B going from the lower left to the upper right is thereby formed in the inside of the cylinder.

Further, as shown in FIG. 6C, in the case of the volume antenna 200 where the number of the straight portions 211 is 12, the wave number of the standing wave is 5, and therefore the number of the nodes is 10. Therefore, when the feed point 204 is provided at the middle point of one straight portion 211, the electric current flows in the straight portions 211 other than straight portion 211 having the feed point 204 and the straight portion 211 at the position 180 degree rotational symmetric with respect to the center axis of the cylinder, among the 12 straight portions 211, in the directions indicated with the arrows shown in the drawing. And a uniform magnetic field B going from the lower left to the upper right is thereby formed in the inside of the cylinder.

As described above, when the number of the straight portions 211 is 4, 6, 8 or 12, if the number of the straight portions 211 is represented as 2N, and the frequency of the electromagnetic wave transmitted and received is such a frequency that a standing wave having a wave number of N−1 is generated in the volume antenna 200, a uniform magnetic field is formed in the inside of the cylinder. Also when the wave number is N+1, directions of the electric current flowing in facing rungs are inverse to each other with respect to the direction of the central axis, as in the case where the wave number is N−1. Therefore, in the volume antenna 200, a magnetic field with almost mirror symmetry with respect to a plane including the feed point 204 and the central axis of the cylinder (henceforth called feed surface) is formed in both portions of the volume antenna 200 on both sides of the feed surface, and thus a uniform magnetic field is formed in the inside of the cylinder.

Moreover, even when the number of the straight portions 211 is 10 or 14 or more, as in the case explained above, a uniform magnetic field is generated in the inside of the cylinder of the volume antenna 200 of this embodiment for an electromagnetic wave generating a standing wave having a wave number n of N±1, when the number of the straight portions 211 of the volume antenna 200 is represented as 2N, and thus the volume antenna 200 operates as the volume antenna of the MRI device 100.

Therefore, if the length L of the ribbon-shaped conductor 201 of the volume antenna 200, where the number of the straight portions 211 of the ribbon-shaped conductor 201 is 2N, is adjusted so as to satisfy the following formulas (3), where fh represents a nuclear magnetic resonance frequency at which the resonance is desired (resonance frequency), the volume antenna 200 operates as the volume antenna of the MRI device 100.

$$L=(N\pm1)\times A\times c/fh \qquad (3)$$

As explained above, if the length of the ribbon-shaped conductor 201 is set as described above, the volume antenna 200 of this embodiment can be used as an RF coil of an MRI device without using a capacitor. Therefore, it can reduce the production cost and maintenance cost. Furthermore, as described above, the length L of the ribbon-shaped conductor 201 can be adjusted by changing the length of the straight portions 211 when it is disposed. Therefore, it can show such flexibility for design that the antenna sensitivity can be adjusted within a wide frequency range regardless of the size of the cylindrical shape serving as the base frame to constitute both of antenna for the head and body coil.

According to this embodiment, there can be provided an RF coil for MRI device free from limitation on possible size of applicable object and allowing reduction of production and maintenance costs.

The resonance frequency fh of the volume antenna 200 of this embodiment varies in proportional to the specific propagation velocity A as indicated by the equation (3). Therefore, by changing the specific propagation velocity A, the resonance frequency fh can also be adjusted. That is, as the relative permittivity $\in_r$ of the material used for the housing 203 is made larger, the resonance frequency can be made lower. When the relative permittivity of the housing 203 is $\in_r$, the specific propagation velocity A with respect to the velocity of light in vacuum c is about $1/\sqrt{(\in_r)}$. Since the relative permittivity $\in_r$ of the material used for the housing 203 is usually about 2 to 4, the specific propagation velocity takes a value of about 0.7 to 0.5. However, this value is an estimated value for an ideal case where all the ribbon-shaped conductor 201 and the cylindrical conductor 202 serving as the ground plane are surrounded by and buried in a dielectric material, the ribbon-shaped conductor 201 has a straight shape, and the ground plane has a planar shape. When the dielectric material exists only at the position between the ground plane (cylindrical conductor 202) and the ribbon-shaped conductor 201, the ground plane (cylindrical conductor 202) has a cylindrical shape, and the ribbon-shaped conductor 201 is curved as in this embodiment, the specific propagation velocity with respect to the velocity of light in vacuum c becomes larger than $1/\sqrt{(\in_r)}$, and closer to 1 in many cases.

Although the ribbon-shaped conductor 201 of the volume antenna 200 of this embodiment is desirably formed so that the lengths of the straight portions 211 are the same, the shape of the conductor is not limited to such a shape. For example, so long as it is formed in such a shape in four-fold rotational symmetry that when it is rotated by 90 degrees around the central axis of the cylinder, the shape is the same as that before the rotation, the lengths of the straight portions 211 may be different from one another. In particular, when the electricity receiving and feeding scheme called QD (Quadrature Detection or Quadtature Drive) electricity receiving and feeding for generating a rotating magnetic field is used, and such a symmetric shape as mentioned above is preferred. In addition, the ribbon-shaped conductor 201 may also be formed so that the shape thereof is in such two-fold rotational symmetry that when it is rotated by 180 degrees around the central axis of the cylinder, the shape is the same as that before the rotation, and also in mirror symmetry with respect to a plane including the central axis.

The same shall apply to the lengths of the arc portions 212, and it is desirable that the arc portions 212 have the same lengths. However, the lengths are not limited to such lengths as mentioned above. Like the straight portions 211, length of the arc portions may be different from one another, as long as the shape of the ribbon-shaped conductor is formed in such two-fold rotational symmetry and mirror symmetry, or four-fold rotational symmetry.

The housing 203 and the cylindrical conductor 202 of the volume antenna 200 of this embodiment are configured to have a cylindrical shape. However, the configuration is not limited to the above configuration. For example, they may constitute a cylinder having an elliptical section. In this case, the arc portions 212 may be configured so as to have a smaller length as the distance from the major axis of the cross-sectional ellipse increases.

Further, although this embodiment was explained by exemplifying a case where the feed point 204 is formed on the straight portion 211, the position of the feed point 204 is not limited to such a position, and it may be provided on the arc portion 212. However, the sensitivity profile of the volume coil 200 of this embodiment changes depending on the position of the feed points 204. Therefore, a position providing a sensitivity profile showing good symmetry is desirable.

Further, in this embodiment, the frequency at which the ribbon-shaped conductor 201 resonates depends on the length L of the ribbon-shaped conductor 201. Therefore, the ribbon-shaped conductor 201 may be configured so as to have further larger degree of freedom for the length L. In this embodiment, the ribbon-shaped conductor 201 is made up of a plurality of the straight portions 211 and the arc portions 212 connecting them. By changing the shape of the straight portions 211, degree of freedom for adjustment of the length L can be further increased. Hereafter, a modified example in which degree of freedom for adjustment of the length L of the ribbon-shaped conductor 201 is increased will be explained.

Figure 7:
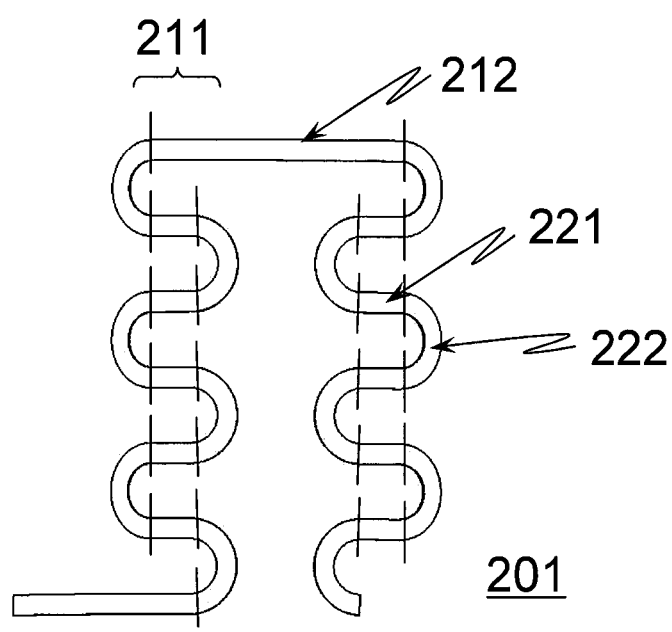
FIG. 7 shows a part of the ribbon-shaped conductor according to a modified embodiment of the present invention.
Figure 8:
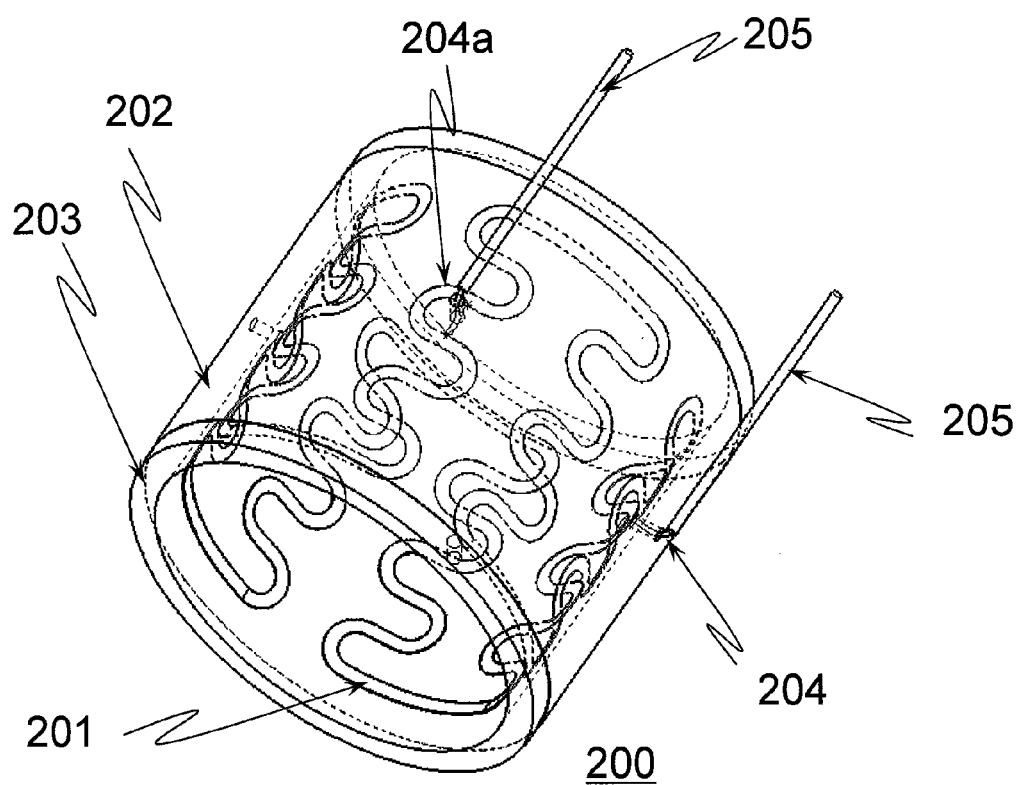
FIG. 8 is a drawing for explaining a modified example of disposition of the ribbon-shaped conductor according to an embodiment of the present invention.

A modified example of the disposition of the ribbon-shaped conductor 201 is shown in FIG. 7. As shown in this drawing, in this modified example, the straight portions 211 is provided with a plurality of second straight portions 221 bended along with the circular arcs of the cross sections perpendicular to the central axis of the housing 203, and second arc portions 222 connecting them in the central axis direction. FIG. 8 is an external view of a volume antenna constituted by the ribbon-shaped conductor of this modified example having 8 of the straight portions 211. The second straight portions 221 have such a length that they do not protrude from the positions of the second arc portions 222 of the adjacent straight portions 211. With such a configuration, the effectual length of the length L of the ribbon-shaped conductor 201 can be lengthened, and the frequency at which a standing wave is generated can be made lower. Therefore, the range of the frequency to which the volume antenna 200 of this embodiment can be applied can be widened.

The method for making the lengths of the straight portions 211 longer is not limited to that of the aforementioned modified example. It is sufficient that a part of it is meandered along the pathway of the straight portions 211 and the arc portions 212. For example, it may have a zigzag shape. However, it must be meandered so that a component of one straight portion 211 in the circumferential direction of the cylinder section does not overlap with a similar component of the adjacent straight portion 211.

Further, although this embodiment was explained by exemplifying a case where one feed point 204 is provided, the number of the feed point 204 is not limited to that number. For example, two of the feed points 204 may be provided. FIG. 8 mentioned above shows an example where two of the feed points 204 are provided. In this drawing, the feed point 204a is the second feed point. Hereafter, the feed point 204 is called the first feed point 204, and the feed point 204a is called the second feed point 204a. FIG. 8 shows an example where the second feed point 204a is disposed at a symmetric position defined by rotating the first feed point 204 by 90 degrees around the axis of the cylinder. However, the positional relationship of the first feed point 204 and the second feed point 204a is not limited to such a relationship.

As explained above, the feed point defines the position of node of a standing wave generated in the ribbon-shaped conductor 201. Further, when a capacitor is disposed as described later, the position of the capacitor is also a position of node in many cases. Therefore, the second feed point 204a can be provided between positions of nodes providing a desired wave number of the standing wave of the frequency to be used. With such a configuration, the volume antenna 200 of this embodiment can generate not only a linearly polarized component of the magnetic field, but also a circularly polarized component, which is efficient for MRI measurement, in the inside of the cylinder.

Further, the volume antenna 200 of this embodiment may also be configured so that a predetermined number of capacitors are disposed to control the resonance frequency.

Figure 9:
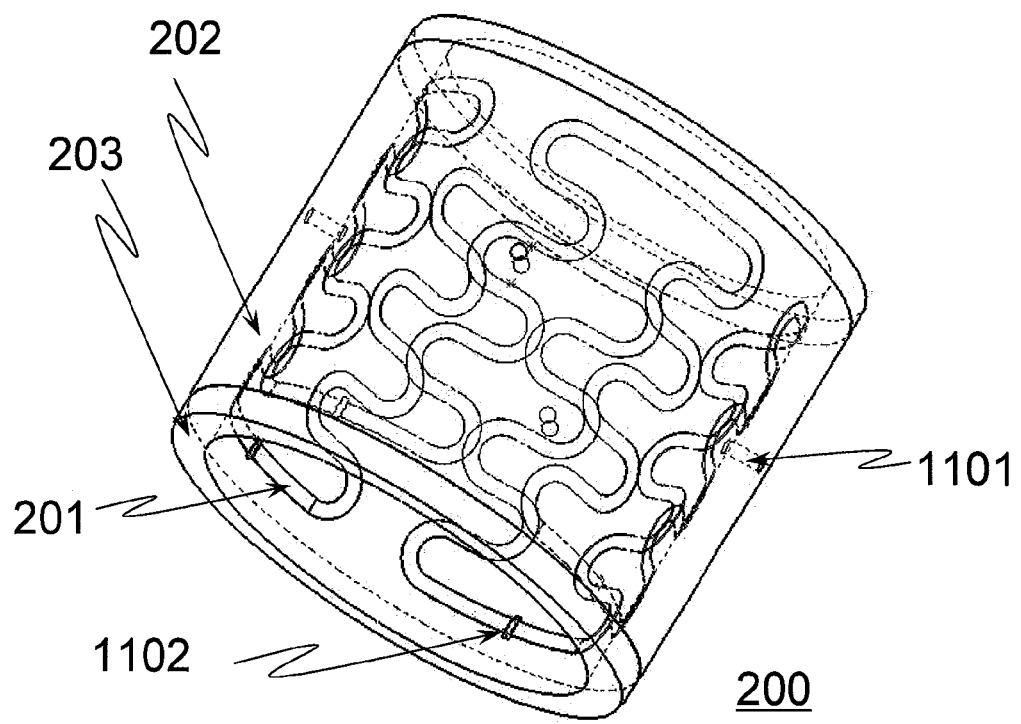
FIG. 9 is a drawing showing structure of a volume antenna according to an embodiment of the present invention in which capacitors are disposed.

FIG. 9 shows the structure of the volume antenna 200 in which capacitors are disposed. If capacitors are disposed at several positions between the ribbon-shaped conductor 201 and the cylindrical conductor 202 as the ground plane, the phase of the radio frequency wave flowing in the ribbon-shaped conductor advances at the position of each capacitor, and thus the same effect as that obtained by effectually elongating the length of the ribbon-shaped conductor can be obtained. Therefore, the resonance frequency of the volume antenna 200 is lowered. Specifically, for example, as shown in FIG. 9, holes 1101 are provided at several positions (for example, 4 positions) between the ribbon-shaped conductor 201 and the ground plane (cylindrical conductor) 202, and capacitors are disposed there.

Further, if capacitors are disposed on the conductor portions of the ribbon-shaped conductor 201, the phase of the radio frequency wave flowing in the ribbon-shaped conductor delays at the positions of the capacitors, and the same effect as that obtained by effectually shortening the length of the ribbon-shaped conductor can be obtained. Therefore, the resonance frequency of the volume antenna 200 can be increased. Specifically, for example, as shown in FIG. 9, gaps (breaks) 1102 are provided at several positions in the middle of the ribbon-shaped conductor 201, and capacitors are disposed there. For example, if capacitors having a capacity of about 50 pF are disposed, the frequency is increased by about 7%. If the capacity of the capacitors is made smaller to, for example, about 10 pF, the increasing ratio of the resonance frequency becomes still larger than the 7%.

Figure 10:
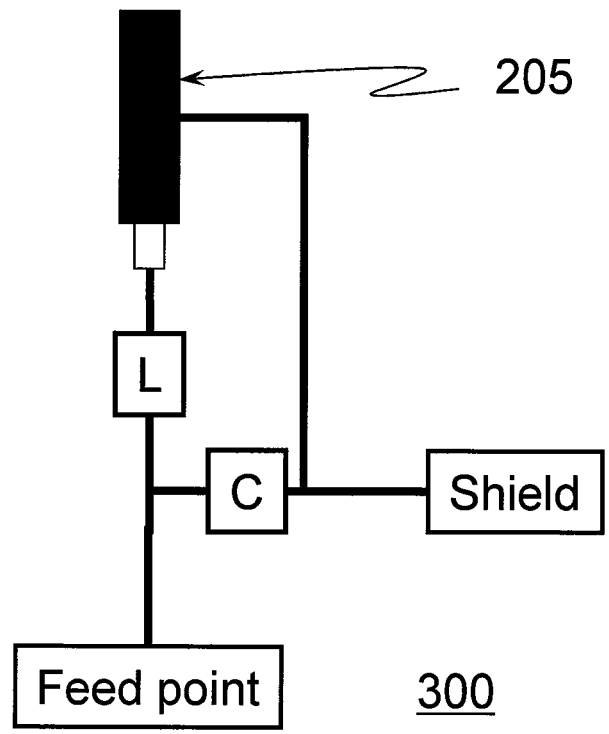
FIG. 10 is a circuit diagram of an impedance matching circuit used in an embodiment of the present invention.

Further, when imaging is performed by using the MRI device 100 connected with the volume antenna 200, impedance matching may be performed, in which impedance Za of the volume antenna 200 is matched with characteristic impedance Zc (for example, 50Ω) of the coaxial cable 205 at the operating frequency (for example, 128 MHz). In this example, an LC circuit 300 is used for the impedance matching. FIG. 10 is a circuit diagram of the LC circuit 300. The coaxial cable 205 is connected to the ribbon-shaped conductor 201 via the LC circuit 300 in the neighborhood of the feed point 204. In FIG. 10, the indication "Feed point" means the feed point 204, and "Shield" means the cylindrical conductor 202. As shown in this drawing, in the LC circuit 300, an inductance L is disposed between the inner conductor of the coaxial cable 205 and the feed point 204, and capacitance C is disposed between the outer conductor of the coaxial cable 205 and the feed point 204. By performing impedance matching by using such an LC circuit 300 as mentioned above, noises can be reduced, and thus image quality of images obtained with the MRI device 100 is improved.

Figure 11:
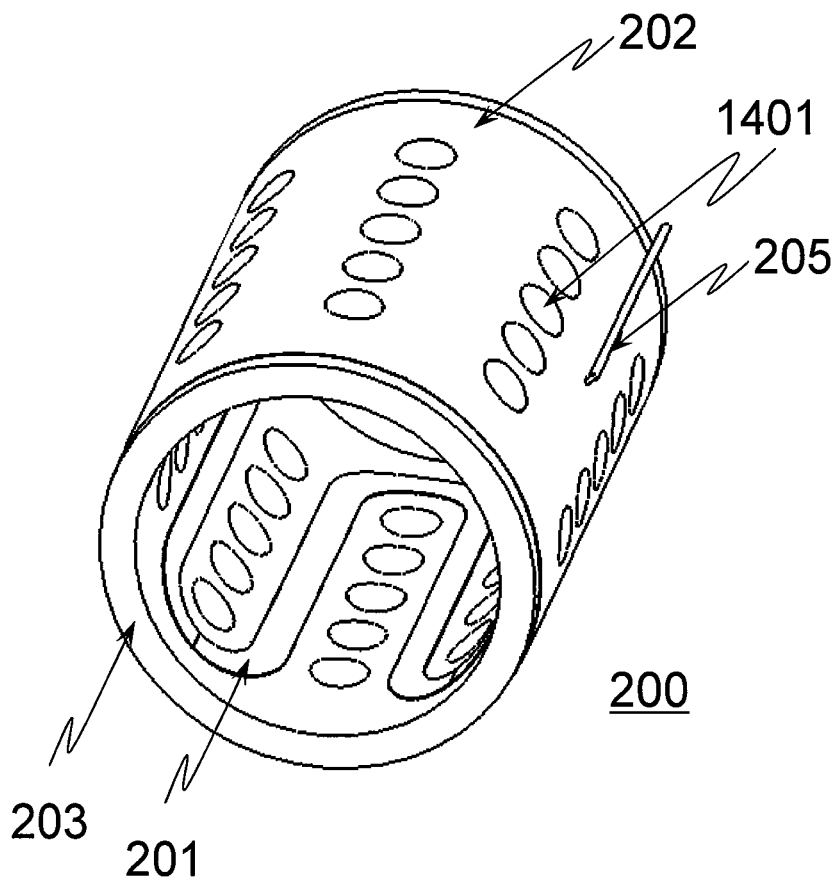
FIG. 11 is a drawing for explaining another example of volume antenna according to an embodiment of the present invention.

Further, in this embodiment, the cylindrical conductor 202 of the volume antenna 200 is formed with, for example, a copper sheet. However, the cylindrical conductor 202 may be formed with a material other than materials in the form of a sheet. For example, as shown in FIG. 11, a plurality of circular holes 1401 may be provided in the housing 203 and the cylindrical conductor 202. It is desirable that the holes 1401 are provided at positions that do not overlap with the ribbon-shaped conductor 201 disposed in the inside of the cylinder. Further, the holes 1401 are provided so that the holes 1401 do not combine due to unduly large area of the holes 1401. This is because if the holes are combined, the function of the cylindrical conductor 202 as the ground plane is degraded. If the volume antenna 200 provided with such holes that they do not degrade the function of the cylindrical conductor is used, comfort is increased, when the human head is entered into the inside of the cylinder as a subject, without significantly changing the characteristics of the antenna compared with the case not providing the holes, and thus favorable results can be obtained.

Further, although not shown as a drawing, the cylindrical conductor 202 may be formed with a copper mesh instead of a copper sheet. Use of a copper mesh does not degrade the function of the cylindrical conductor 202 as the ground plane. Therefore, comfort for the human subject can be increased with maintaining the function of the volume antenna 200. In particular, when the volume antenna 200 is used for the human head, closed feeling of the human subject can be reduced.

Figure 12:
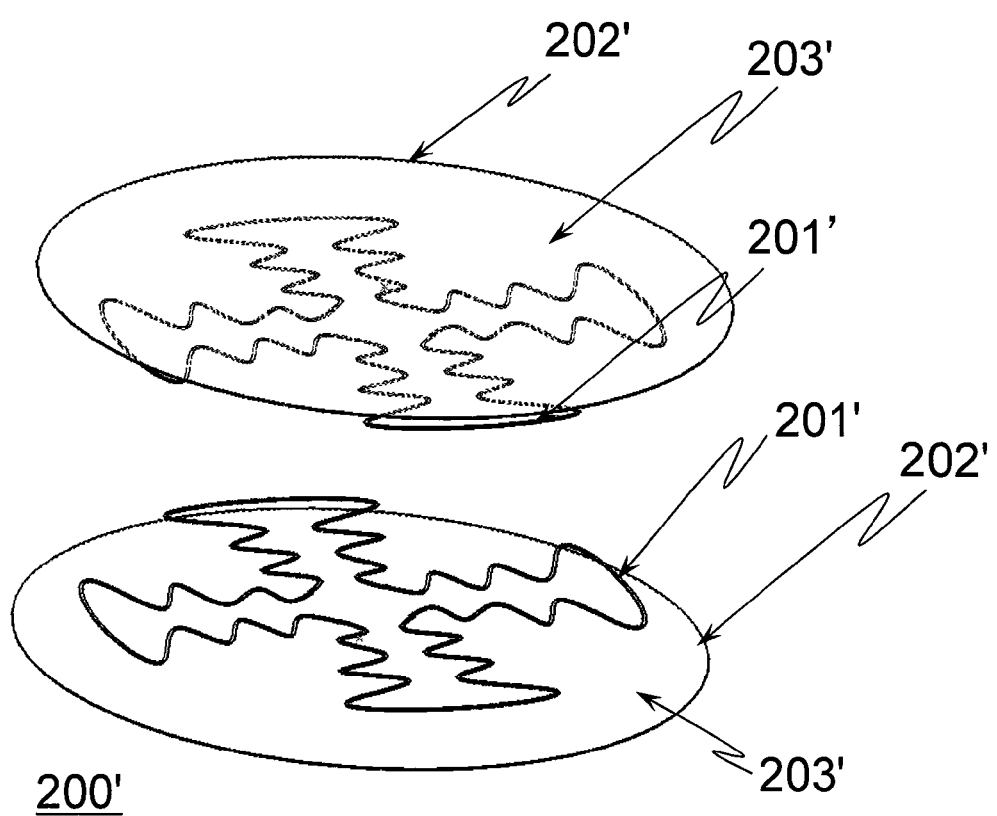
FIG. 12 shows a configuration of MRI device of vertical magnetic field type using a volume antenna according to an embodiment of the present invention.

Further, although this embodiment was explained by exemplifying the MRI device 100 of the horizontal magnetic field type where the magnet 101 has a cylindrical shape, the MRI device 100 may be of the vertical magnetic field type as described above. A configurational diagram of a volume antenna 200' for the MRI device 100 of the vertical magnetic field type is shown in FIG. 12.

The MRI device 100 of the vertical magnetic field type has a configuration that the magnet 101 is provided with a pair of magnets disposed up and down on both sides of the subject. For the disposition in the space formed by this magnet 101, the volume antenna 200' is provided with a pair of conductors having a disc shape (disc-shaped conductors) 202', housings 203' and ribbon-shaped conductors 201' instead of the cylindrical conductor 202 and the housing 203 of the volume antenna 200.

The ribbon-shaped conductors 201' are each disposed in such a widely extended plane shape as an umbrella on each of facing surfaces of a pair of the housings 203'. Each of the ribbon-shaped conductors 201' in this pair is formed in the shape of loop. Further, the ribbon-shaped conductor 201' is provided with a plurality (even number) of straight portions and arc portions. The straight portions may be further provided with a plurality of second straight portions and second arc portions. A feed point is provided in each of the disc-shaped conductors 202' and the ribbon-shaped conductors 201' in the aforementioned pair.

In the MRI device 100 of the vertical magnetic field type, among the aforementioned one pair of elements, one set of the ribbon-shaped conductor 201', the disc-shaped conductor 202' and the housing 203' is disposed under the upper magnet of the magnet 101, and the other set is disposed over the lower magnet of the magnet 101 so as to face the foregoing set. The volume antenna 200' generates a magnetic field in the space between these sets in a direction parallel to the planes of the disc-shaped conductor 202' and the housing 203', and has sensitivity in the space. Therefore, a subject is placed in this space and an image is obtained.

In addition, also in the volume antenna 200', by providing feed points at two positions in disc-shaped conductor 202' and ribbon-shaped conductors 201' of the upper and lower sets, a circularly polarized component can be generated.

The volume antenna 200 of this embodiment can be used in not only the RF coil 103 of MRI devices, but also all instruments using electromagnetic waves having a frequency of from several MHz to several GHz.

EXAMPLE

There will be explained an example of the volume antenna 200 according to the embodiment explained above for the case of using it as a volume antenna for the head of an MRI device used at a magnetic field intensity of 3 teslas (henceforth referred to as MRI device of 3 teslas). The imaging nuclide was hydrogen nucleus. The housing 203 was formed with a transparent acrylic resin showing a relative permittivity $\in_r$ of about 2.6 in such a size that the human head could be entered in it. Specifically, the internal diameter was 280 mm, the external diameter was 320 mm, and the length was 270 mm.

On the external side surface of the cylinder of the housing 203, a copper foil (copper sheet) having a thickness of 35 μm was adhered as the cylindrical conductor 202. Two of the copper foils having a length of 270 mm in the direction of the axis of the cylinder and a developed length of 600 mm for the circumferential direction were piled up and adhered on the housing 203 with a double-sided adhesive tape. The piled two sheets of the foils were adhered in the circumferential direction in order to suppress an electric current of the circumferential direction of the cylinder called eddy current that compensates gradient magnetic field of about several MHz at the maximum. If such an eddy current flows, image noises increase. In addition, since two of the copper sheets were adhered in a large area with the double-sided adhesive tape, there was obtained a function equivalent to that obtained by connecting them with a capacitor of several hundreds of pF, and thus they could be regarded as a ground plane in one continuous cylindrical shape at the magnetic resonance frequency (resonance frequency) $f_H$ of the hydrogen nucleus at 3 teslas (about 128 MHz).

The material of the ribbon-shaped conductor 201 was also a copper foil having a thickness of 35 μm, and such a copper foil was cut into the shape shown in FIG. 7 with a cutter knife, and adhered on the internal surface of the housing 203 with a double-sided adhesive tape. The ribbon-shaped conductor 201 had a width of 10 mm, and the length of the second straight portions 221 of the ribbon-shaped conductor was 21 mm, and the radius of the second arc portions 222 was 18.5 mm. Further, the number of the straight portions 211 (made up of the first straight portions 221 and the second arc portions 222) corresponding to rungs was eight.

Figure 13:
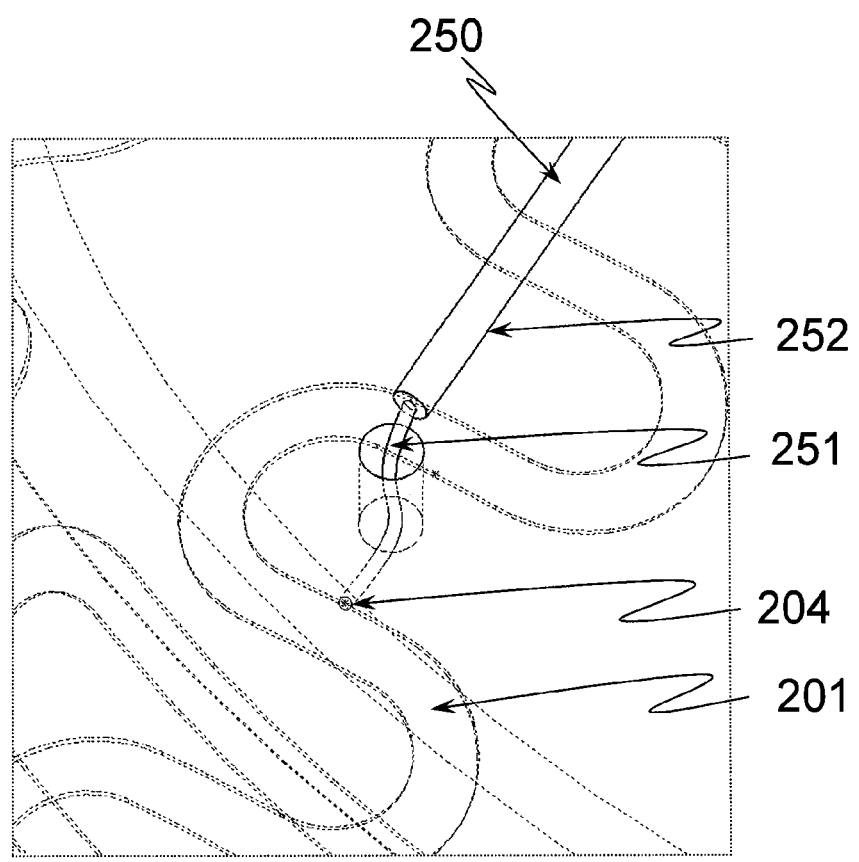
FIG. 13 is a drawing showing details of a feed point according to an embodiment of the present invention.

In order to measure the impedance characteristic of the volume antenna 200, an outer conductor of one coaxial cable 205 was soldered to the cylindrical conductor 202, and a inner conductor of the coaxial cable 205 was connected to the ribbon-shaped conductor 801. FIG. 13 shows the details of the connection part of the coaxial cable 205 (feed point 204).

The inner conductor 251 of the coaxial cable 205 was passed through holes provided in the housing 203 and the cylindrical conductor 202, and connected to the ribbon-shaped conductor 201 in the inside at the feed point 204. The outer conductor 252 of the coaxial cable 205 was electrically connected to the cylindrical conductor 202 by soldering near the position at which the inner conductor 251 of the coaxial cable 205 was introduced into the inside of the housing 203.

Figure 14:
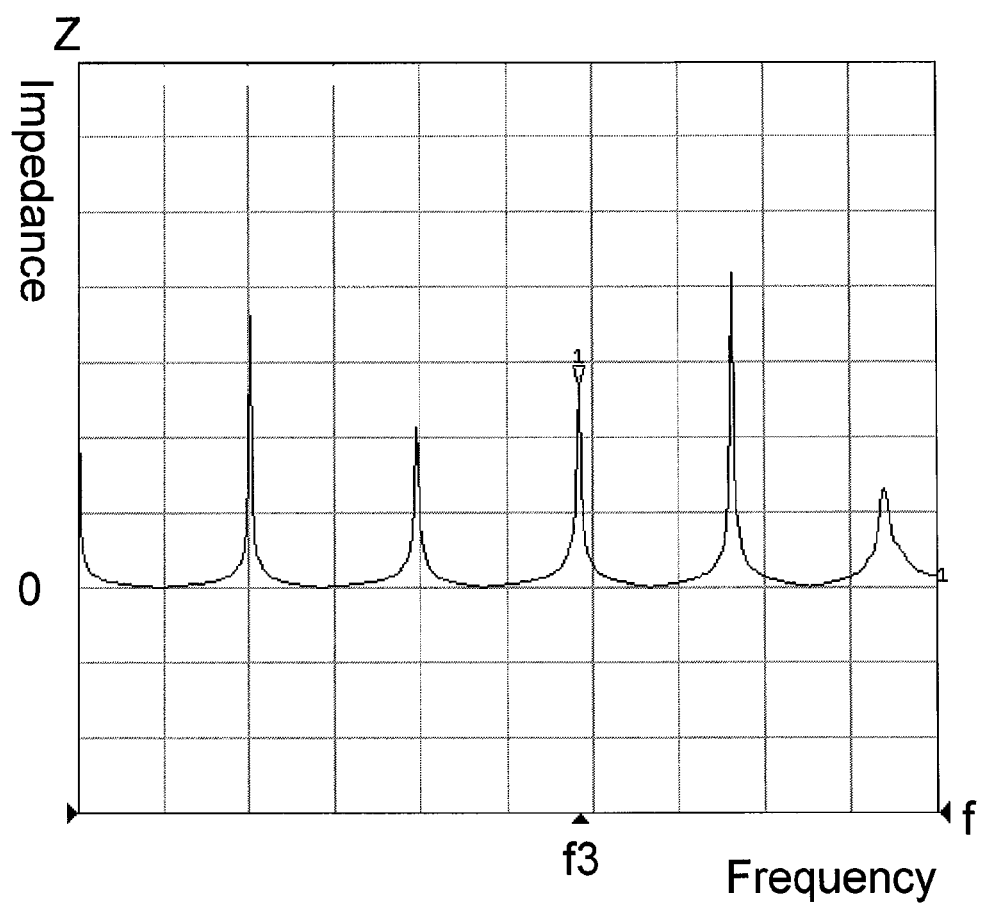
FIG. 14 shows results of measurement of impedance in an example of the present invention.

The results of measurement of the impedance Z performed in this state with sweeping the frequency are shown in FIG. 14. In this graph, the vertical axis indicates magnitude of the impedance Z, the horizontal axis indicates the frequency f, and there was obtained a curve comprising peaks of high impedances Z (resonance peaks) locating along the horizontal axis at substantially equal intervals. In this graph, the frequencies f showing high impedances Z are frequencies f at which the volume antenna 200 resonates, and frequencies at which a standing wave was generated. The frequency f3 of the third resonance peak from the lower frequency side showing uniform sensitivity as a volume antenna for MRI devices was about 146 MHz.

Since the resonance frequency of the nuclide for imaging was about 128 MHz as described above, the resonance peak at 146 MHz was lowered by about 12% and thereby adjusted to 128 MHz. For this purpose, for example, the straight portions 211 of the ribbon-shaped conductor 201 may be lengthened by increasing the number of meandering of the ribbon-shaped conductor 201 so as to lengthen the total length of the ribbon-shaped conductor 201 by about 12%. As described above, capacitors may be provided at several positions between the ribbon-shaped conductor 201 and the cylindrical conductor 202 as the ground plane to lower the resonance frequency. In this example, as shown in FIG. 9, capacitors of 17.5 pF were connected through 4 of the holes 1101, respectively. Then, the resonance peak of 146 MHz shifted to around 128 MHz. As a result, the frequency became equal to the frequency used in the MRI device of 3 teslas, and the antenna was made to be an antenna that could be used for imaging.

In this example, impedance matching was performed by using the circuit shown in FIG. 10 in a state that a container of almost water (phantom) instead of the human head was placed in the inside of the antenna. Specifically, the impedance peak in this state was 380Ω, and for matching 380Ω to 50Ω, an inductance L of about 180 nH and a capacitor C of about 7 pF were inserted.

Figure 15:
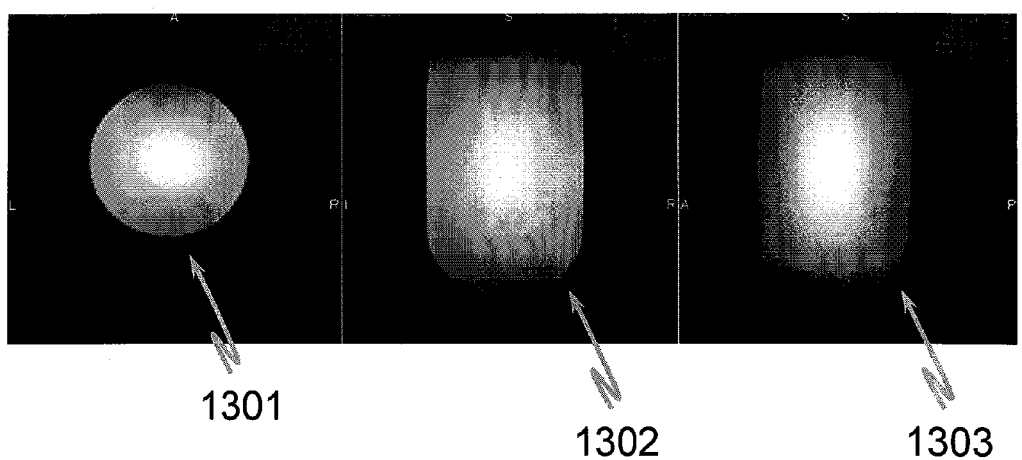
FIG. 15 includes images obtained in an example of the present invention.

The images obtained by manufacturing a head volume antenna for a 3 tesla MRI system in such a manner as described above, and performing imaging of a phantom are shown in FIG. 15. In this example, a cylindrical container having a diameter of 149 mm and a length of 250 mm and mainly containing 3.8 kg of water was used as the phantom. The images include those of the axial section 1301, coronal section 1302, and sagittal section 1303. It can be seen that favorable uniform images were obtained for all the sections.

Denotation of Reference Numerals

100: MRI apparatus, 101: magnet, 102: gradient coil, 103: RF antenna, 104: transceiver, 105: data processing part/operation part, 106: transmission and reception cable, 107: gradient magnetic field control cable, 108: display, 109: gradient magnetic field power supply, 200: volume antenna, 200': volume antenna, 201: ribbon-shaped conductor, 201': ribbon-shaped conductor, 202: cylindrical conductor, 202': disc-shaped conductor, 203: housing (dielectric material), 203': housing, 204: feed point, 204a: second feed point, 205: coaxial cable, 211: straight portion, 212: arc portion, 221: second straight portion, 222: second arc portion, 251: inner conductor, 252: outer conductor, 300: LC circuit, 801: node, 802: node, 803: node, 804: node, 805: node, 806: node, 811: direction of electric current, 821: straight portion, 822: straight portion, 823: straight portion, 824: straight portion, 825: straight portion, 826: straight portion, 827: straight portion, 828: straight portion, 831: direction of magnetic field, 832: direction of magnetic field, 851: node, 852: node, 853: node, 854: node, 855: node, 856: node, 857: node, 858: node, 859: node, 860: node, 861: direction of electric current, 871: direction of magnetic field, 872: direction of magnetic field, 1101: hole, 1102: gap, 1301: axial section, 1302: coronal section, and 1303: sagittal section

The invention claimed is:

1. An RF antenna device of an MRI apparatus used for transmission and/or reception of a signal, comprising:

a cylindrical conductor having a cylindrical shape;

a ribbon-shaped conductor having a length longer than the circumference of the cylindrical conductor; and a cable connected to the cylindrical conductor and the ribbon-shaped conductor, which transmits and receives signals to and from the RF antenna device, wherein the ribbon-shaped conductor is disposed on a cylindrical surface inside of the cylindrical conductor in the form of a loop so as to generate a magnetic field having a component perpendicular to a central axis of the cylindrical conductor in the inside of the cylindrical conductor, the ribbon-shaped conductor comprises:

a plurality of first portions having a component parallel to the central axis direction of the cylindrical conductor, and a plurality of second portions having a component in the circumferential direction of the cylindrical conductor connecting the first portions, wherein the first portions are disposed so that a component along the circumferential direction of the cylindrical conductor of one first portion does not overlap with a component along the circumferential direction of the cylindrical conductor of an adjacent first portion, and where a number of the first portions of the ribbon-shaped conductor is represented as 2N (where N is equal to a wavenumber of an electromagnetic wave to be transmitted or received), a length of the ribbon-shaped conductor is represented as L, and a specific propagation velocity ratio of the whole propagation line of the ribbon-shaped conductor with the cylindrical conductor as a ground plane, with respect to the velocity of light in a vacuum, is represented as A, a value obtained by dividing the length L by the specific propagation velocity ratio A is substantially equal to (N−1) or (N+1) times the wavelength of an electromagnetic wave in a vacuum that resonates with the antenna device.

2. The RF antenna device according to claim 1, wherein: the first portions are straight lines parallel to the central axis direction of the cylindrical conductor.

3. The RF antenna device according to claim 2, wherein: all of the plurality of the first portions have the same length.

4. The RF antenna device according to claim 2, wherein: all of the plurality of the second portions have the same length.

5. The RF antenna device according to claim 1 comprising: a dielectric material having a relative permittivity of 1 or larger is disposed between the cylindrical conductor and the ribbon-shaped conductor.

6. The RF antenna device according to claim 1, wherein: the cable further comprises:
a matching circuit for matching impedance of the antenna device with impedance of the cable at a frequency of an electromagnetic wave that resonates with the antenna device.

7. The RF antenna device according to claim 1, wherein: a capacitor is connected between the cylindrical conductor and the ribbon-shaped conductor.

8. The RF antenna device according to claim 1, wherein: the ribbon-shaped conductor has a gap in the ribbon-shaped conductor, and a capacitor is disposed in the gap.

9. The RF antenna device according to claim 1, wherein: the first portions of the ribbon-shaped conductor have a connecting point to which the cable is connected.

10. The RF antenna device according to claim 9, wherein: the first portions of the ribbon-shaped conductor further comprise a second connecting point to which the cable is connected, and
the second connecting point is located at a position defined by rotating the connecting point by 90 degrees around the central axis of the cylinder.

11. The RF antenna device according to claim 1, wherein: the cylindrical conductor has a hole.

12. The RF antenna device according to claim 1, wherein: the cylindrical conductor is formed with a metal mesh.

13. A magnetic resonance imaging device comprising a static magnetic field generator that generates a static magnetic field, an RF coil that is disposed in a space of the static magnetic field generated by the static magnetic field generator and generates a radio frequency magnetic field of a direction perpendicular to the direction of the static magnetic field or detects a radio frequency magnetic field of a direction perpendicular to the direction of the static magnetic field, and an imaging device that images internal information of a subject by using nuclear magnetic resonance signals generated from the subject placed in the space of the static magnetic field and detected by the RF coil, wherein:
the magnetic resonance imaging device comprises the antenna device according to claim 1 as the RF coil.

* * * * *